United States Patent

Matsuzaki et al.

[11] Patent Number: 5,849,834
[45] Date of Patent: Dec. 15, 1998

[54] W/O TYPE EMULSIFIED COMPOSITION AND COSMETIC

[75] Inventors: Fumiaki Matsuzaki; Toshio Yanaki; Michihiro Yamaguchi, all of Yokohama, Japan

[73] Assignee: Shiseido Co., Ltd., Tokyo, Japan

[21] Appl. No.: 814,183

[22] Filed: Mar. 10, 1997

[30] Foreign Application Priority Data

Mar. 12, 1996 [JP] Japan .................................. 8-055180
Mar. 12, 1996 [JP] Japan .................................. 8-055181

[51] Int. Cl.⁶ ................................................. C08J 3/00
[52] U.S. Cl. ..................... 524/522; 525/201; 525/217; 525/296; 526/240; 526/303.1; 526/320
[58] Field of Search ................... 524/522; 525/296, 525/201, 217; 526/320, 303.1, 240

[56] References Cited

U.S. PATENT DOCUMENTS

| | | | |
|---|---|---|---|
| 4,443,576 | 4/1984 | Bhattacharyya et al. | 524/522 |
| 4,686,099 | 8/1987 | Palinczar | 424/47 |
| 5,051,305 | 9/1991 | Whitaker, Sr. | 428/402.2 |
| 5,059,414 | 10/1991 | Dallal et al. | 424/60 |
| 5,332,595 | 7/1994 | Gaonkar | 426/602 |

FOREIGN PATENT DOCUMENTS 0287105A 4/1988 European Pat. Off. .

OTHER PUBLICATIONS

Patent Abstracts of Japan, vol. 003, No.003 (C–003), 1–16–79, and JP 53 127836 A (Kanebo Ltd.), 8 Nov. 1978.
Patent Abstracts of Japan, vol. 003, No. 068 (C–048), 13 Jun. 1979, and JP 54 043210 A (Lion Corp.), 5 Apr. 1979.

*Primary Examiner*—Terressa Mosley
*Attorney, Agent, or Firm*—Townsend & Banta

[57] ABSTRACT

A W/O type emulsified composition comprising an oil phase containing ethyl cellulose and a solvent capable of swelling ethyl cellulose and a water phase containing a water soluble polymer(s) emulsified as a water-in-oil type (W/O type) emulsion. A W/O type emulsified composition comprising an oil phase containing ethyl cellulose and a solvent capable of swelling ethyl cellulose and a water phase containing a polyion complex comprising cationized cellulose and sodium hyaluronate emulsified as a water-in-oil type (W/O type) emulsion.

10 Claims, No Drawings

W/O TYPE EMULSIFIED COMPOSITION AND COSMETIC

RELATED APPLICATION

This application claims the priority of Japanese Patent applications No.8-55180 filed on Mar. 12, 1996 and No.8-55181 filed on Mar. 12, 1996, which is incorporeted herein by reference.

BACKGROUND OF THE INVENTION

1. Field of the Invention

This invention relates in general to a W/O type emulsified composition, a method of manufacturing it as well as a W/O type emulsified cosmetic which uses it, and more particularly to a W/O type emulsified composition which is emulsified without using conventional low molecular weight surfactants and is stable, safe and easy to use, a method of manufacturing it as well as a W/O type emulsified cosmetic which uses it.

2. The Prior Art

Conventionally, a great deal of research has been conducted on emulsification, and many emulsifiers have been developed. The progress of emulsification technology has also been remarkable, and very stable emulsions have been widely used in every industry. However, most of them employ as the emulsifier a non-ionic surfactant containing polyoxyethylene chains, an anionic surfactant such as aliphatic soap or an imidazoline or betaine type ampholytic surfactant, and many people, particularly general consumers, are concerned about safety.

Therefore, in recent years, attempts have been made to use water soluble polymers for the emulsifier because they are believed to be safer. However, compared with surfactants such as the aforementioned non-ionic surfactant, water soluble polymers are less able to reduce the surface tension and therefore they have a relatively small emulsifying ability, resulting in poor emulsification stability. Also, since the emulsification system is easily destroyed at the time of application, absorption into the skin is poor and sometimes repulsion is observed.

In view of the aforementioned problems, the inventors conducted earnest research and discovered that a W/O type emulsified composition with excellent emulsification stability could be obtained, without using conventional surfactants, by stirring together an oil phase which contained ethyl cellulose and a solvent capable of swelling ethyl cellulose and a water phase which contained a water soluble polymer or a specific polyion complex, and thus completed the present invention.

BRIEF SUMMARY OF THE INVENTION

The object of the present invention is to provide a W/O type emulsified composition with superior safety characteristics and also superior emulsification stability without using conventional surfactants by means of carrying out emulsification without using conventional surfactants.

The present invention provides a W/O type emulsified composition comprising an oil phase containing ethyl cellulose and a solvent capable of swelling ethyl cellulose and a water phase containing a water soluble polymer(s) emulsified as a water-in-oil type (W/O type) emulsion.

Also, the present invention provides said W/O type emulsified composition wherein said solvent capable of swelling ethyl cellulose is one or more types of solvent chosen from among a group comprising methanol, ethanol, propanol, isopropanol, isobutyl alcohol, benzyl alcohol and acetone.

Also, the present invention provides said W/O type emulsified composition wherein the amount of said ethyl cellulose added is 0.01–10 wt % of the total W/O type emulsified composition, the amount of said solvent capable of swelling ethyl cellulose added is 0.01–20 wt % of the total W/O type emulsified composition, and the amount of said water soluble polymer added is 0.1–10 wt % of the total W/O type emulsified composition.

Also, the present invention provides a W/O type emulsified composition comprising an oil phase containing ethyl cellulose and a solvent capable of swelling ethyl cellulose and a water phase containing a polyion complex comprising cationized cellulose and sodium hyaluronate emulsified as a water-in-oil type (W/O type) emulsion.

Also, the present invention provides said W/O type emulsified composition wherein said solvent capable of swelling ethyl cellulose is one or more types of solvent chosen from among a group comprising methanol, ethanol, propanol, isopropanol, isobutyl alcohol, benzyl alcohol and acetone.

Also, the present invention provides said W/O type emulsified composition wherein the amount of said ethyl cellulose added is 0.01–10 wt % of the total W/O type emulsified composition, the amount of said solvent capable of swelling ethyl cellulose added is 0.01–20 wt % of the total W/O type emulsified composition, and the amount of said polyion complex added is 0.1–10 wt % of the total W/O type emulsified composition.

Also, the present invention provides a method of manufacturing a W/O type emulsified composition in which an oil phase containing ethyl cellulose is prepared by using a solvent capable of swelling ethyl cellulose and then said oil phase and a water phase containing a water soluble polymer are stirred without using a surfactant to emulsify them as a water-in-oil type (W/O type) emulsion.

Also, the present invention provides a method of manufacturing a W/O type emulsified composition in which an oil phase containing ethyl cellulose is prepared by using a solvent capable of swelling ethyl cellulose and then said oil phase and a water phase containing a polyion complex comprising cationized cellulose and sodium hyaluronate are stirred without using a surfactant to emulsify them as a water-in-oil type (W/O type) emulsion.

Also, the present invention provides a W/O type emulsified cosmetic comprising said W/O type emulsified composition.

DETAILED DESCRIPTION

The configuration of the present invention is described in detail below.

The main point of the present invention is to provide a new W/O type emulsified composition with superior emulsification stability without using conventional surfactants. Conventional W/O type emulsified compositions which use a water soluble polymer for the emulsifier have a poor ability to emulsify and poor emulsification stability. However, it was unexpectedly discovered that a new W/O type emulsified composition with excellent emulsification stability could be obtained by adding ethyl cellulose and a solvent capable of swelling ethyl cellulose to the oil phase, leading to completion of the present invention. In the present invention, selection of a special component(s) produced an unexpected effect and provided an advanced new W/O type emulsified composition. Also, unexpected excellent emulsification stability was discovered in a new W/O type emulsified composition in which the oil phase had ethyl cellulose and a solvent capable of swelling ethyl cellulose and the water phase had a polyion complex comprising cationized cellulose and sodium hyaluronate.

Ethyl cellulose (hereafter abbreviated as EC), which is used in the present invention as the oil soluble polymer, is cellulose with some of its three hydroxyl groups substituted by ethoxyl groups. It is preferable to use an ethoxyl group content of 40–50%. EC is first swollen in ethanol and then dissolved or swollen in the oil component typically used in cosmetics, medicinal drugs or food applications. It is also possible to prepare the oil phase by dispersing EC in the oil component and then adding a solvent capable of swelling ethyl cellulose. For highly compatible oils, preferable are methylphenyl polysiloxane, higher alcohols and fatty acids which are liquid at normal temperatures. The amount of EC to be blended is preferably 0.01–10 wt %, more preferably 0.5–5 wt %, of the total W/O type emulsified composition. If it is less than 0.01 wt %, then the visco-elasticity of the continuous phase is low and the emulsification stability deteriorates. If it is more than 10 wt %, then the visco-elasticity of the continuous phase is high and emulsification can be difficult.

The selection of the solvent capable of swelling ethyl cellulose is not limited in particular, but preferable are swelling agents typically used in cosmetics, medicinal drugs and food including methanol, ethanol, propanol, isopropanol, isobutyl alcohol, benzyl alcohol and acetone. The amount of the solvent capable of swelling ethyl cellulose to be blended is preferably 0.01–20 wt % of the total W/O type emulsified composition. It should preferably be equal to or more than the amount of EC to be blended.

The oil components used in the present invention include oil components typically blended in cosmetics such as liquid fats/oils, solid fats/oils, waxes, hydrocarbons, higher fatty acids, higher alcohols, synthetic esters and silicones.

Examples of the liquid fats/oils include avocado oil, tsubaki oil, turtle oil, macadamia nut oil, corn oil, mink oil, olive oil, rape seed oil, egg york oil, sesame seed oil, persic oil, wheat germ oil, sasanqua oil, castor oil, linseed oil, safflower oil, cotton seed oil, perilla oil, soy bean oil, peanut oil, tea seed oil, kaya oil, rice bran oil, chinese wood oil, Japanese wood oil, jojoba oil, germ oil, triglycerol, glyceryl trioctanoate and glyceryl triisopalmitate.

Examples of the solid fats/oils include cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hydrogenated castor oil.

Examples of the waxes include honeybee wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

Examples of the hydrocarbon oils include liquid paraffin, ozokerite, squalene, pristane, paraffin, ceresin, squalene, vaseline and microcrystalline wax.

Examples of the higher fatty acids include lauric acid, myristic acid, palmitic acid, stearic acid, behenic acid, oleic acid, 12-hydroxystearic acid, undecylenic acid, tall oil (sulfated caster oil), isostearic acid, linoleic acid, linolenic acid, eicosapentaenoic acid (EPA) and docosahexaenoic acid (DHA). Higher fatty acids which are liquid at normal temperatures are particularly preferable.

Examples of the higher alcohols include linear chain alcohols including lauryl alcohol, cetyl alcohol, stearyl alcohol, behenyl alcohol, myristyl alcohol, oleyl alcohol and cetostearyl alcohol; and branched chain alcohols including monostearylglycerol ether (batyl alcohol), 2-decyltetradecynol, lanolin alcohol, cholesterol, phytosterol, hexyldodecanol, isostearyl alcohol and octyldodecanol. Higher alcohols which are liquid at normal temperatures are particularly preferable.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester. n-alkyl glycol monoisostearate, neopentyl glycol dicaprylate, diisostearyl malate, glyceryl di-2-heptylundecanoate, trimethylolpropane tri-2-ethylhexylate, trimethylolpropane triisostearate, pentaneerythritol tetra-2-ethylhexylate, glyceryl tri-2-ethylhexylate, trimethylolpropane triisostearate, cetyl 2-ethylhexanoate, 2-ethylhexyl palmitate, glyceryl trimyristate, glyceride tri-2-heptylundecanoate, methyl castor oil fatty acid, oleyl oleate, cetostearyl alcohol, aceto glyceride, 2-heptylundecyl palmitate, diisobutyl adipate, 2-octyldodecyl n-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate.

Examples of the silicones are: chain polysiloxanes including dimethylpolysiloxane, methylphenylpolysiloxane and methylhydrogenpolysiloxane; ring polysiloxanes including decamethylpolysiloxane, dodecamethylpolysiloxane and tetramethyltetrahydrogenpolysiloxane, as well as silicone resin and silicone rubber which form three-dimensional networks.

For the water soluble polymer used in the present invention, any water soluble polymer conventionally used as a thickener and/or emulsification stabilizer is sufficient.

Examples of the natural water soluble polymers are: plant polymers including gum arabic, gum tragacanth, galactan, guar gum, carob gum, karaya gum, carrageenan, pectin, agar, quince seed, algae colloid, starch and glycyrrhizic acid; microbial polymers including xanthangum, dextran, succinoglucane and and animal polymers including collagen, casein and gelatin.

Examples of the semi-synthesized water soluble polymers are: starch type polymers including carboxymethyl starch and methylhydroxypropyl starch; cellulose type polymers including methyl cellulose, methylhydroxypropyl cellulose, hydroxyethyl cellulose, sodium cellulose sulfate, hydroxypropyl cellulose, carboxymethyl cellulose, sodium carboxymethyl cellulose (CMC) and cationized cellulose; alginic acid type polymers including sodium alginate and propyleneglycol alginate ester.

Examples of the synthesized water soluble polymers are: vinyl type polymers including polyvinyl alcohol, polyvinylmethyl ether, polyvinyl pyrolidone and carboxyvinyl polymer; polyoxyethylene type polymers including polyethylene glycols 20,000, 40,000 and 60,000; polyoxyethylene polyoxypropylene copolymer copolymerization type polymer; acrylic polymers including sodium polyacrylate, polyethyl acrylate and polyacryl amide; as well as polyethylene imine and cation polymer.

Examples of the inorganic water soluble polymers include bentonite, AlMg silicate (beegum), laponite, hectorite and anhydrous silicic acid.

Particularly preferable is a water soluble polymer which is not easily affected by salts, such as sodium carboxymethyl cellulose (hereafter abbreviated as CMC). The amount of the water soluble polymer to be blended is preferably 0.1–10 wt %, more preferably 0.5–5 wt %, of the total W/O type emulsified composition. If it is less than 0.1 wt %, then it is not possible to control coalescing of the non-continuous phase, resulting in an unstable emulsified composition. If it is more than 10 wt %, then emulsification can be difficult.

The polyion complex (hereafter abbreviated as PIC) used in the present invention is a complex comprising cationized cellulose (polyquaternium-4, polyquaternium-10 and polyquaternium-24 for example, hereafter abbreviated as CC) and sodium hyaluronate (hereafter abbreviated as HA—Na) which are polymer electrolytes with opposing charges. The complex is formed by adding cationized cellulose and sodium hyaluronate to the water phase. The weight ratio of CC and HA—Na is preferably CC:HA—Na=9.9:0.1–8:2 and more preferably 9:1–8:2. The amount of PIC to be blended is preferably 0.1–10 wt %, more preferably 0.5–5 wt %, of the total W/O type emulsified composition. In the present invention, cationized cellulose and sodium hyaluronate can be directly added to the water phase, or their aqueous solutions can be added to the water phase. The total amount of cationized cellulose and sodium hyaluronate is preferably 0.1–10 wt %, more preferably 0.5–5 wt % of the total emulsified composition. The weight ratio of CC and HA—Na is preferably CC:HA—Na=9.9:0.1–8:2. If the blend ratio is outside of this range the emulsification stability may be reduced.

In the present invention, the ratio of the oil phase and the water phase which constitute the aforementioned W/O type emulsified composition can be chosen from a wide range. A preferable weight ratio of (water phase oil phase) is (40–90/60–10).

The W/O type emulsified composition of the present invention can be prepared by, for example, swelling EC in a solvent capable of swelling EC, adding the oil component and raising the temperature up to 70° C. to prepare the oil phase, or dispersing EC in the oil component, raising the temperature up to 70* and adding a solvent capable of swelling EC to prepare the oil phase, followed by addition of the water phase containing the aforementioned essential ingredients prepared to have a temperature of 70° C. In this case, it is preferable to carry out a vigorous stirring treatment using a homogenizer or disper. Alternatively, after using the solvent capable of swelling EC to prepare the oil phase containing EC, the solvent capable of swelling EC can be distilled away before stirring the oil phase and the water phase together to obtain a W/O type emulsified composition which does not contain the solvent capable of swelling EC. The main point of the method of manufacturing the W/O type emulsified composition of the present invention is to use the solvent capable of swelling EC.

The application of the W/O type emulsified composition of the present invention is not limited. It can be used, for example, in cosmetics, medicinal drugs and food. In addition to the aforementioned essential ingredients, humectants, drugs, ultraviolet light absorbents, preservatives, antioxidants and perfumes can be added to said emulsified composition pertaining to the present invention, and it is preferable to use the product as a W/O type emulsified cosmetic with superior stability, safety characteristics and ease of use.

The present invention makes it possible to provide a W/O type emulsified composition with superior stability, safety characteristics and ease of use without using conventional surfactants, by means of using an oil phase containing ethyl cellulose and a solvent capable of swelling ethyl cellulose and a water phase containing a water soluble polymer or a polyion complex comprising cationized cellulose and sodium hyaluronate.

EXAMPLES

The present invention is further described in detail below by referring to comparative examples and examples. The present invention is not limited to these examples.

(Examples 1–7, Comparative Examples 1–4)

EC, ethanol (a solvent capable of swelling EC), the oil component, purified water, CMC and HA—Na were blended according to the blond composition and amounts shown in Table 1. After heating up the mixture to 70° C., emulsification using a disper was conducted to obtain the emulsified composition. The emulsified composition was observed to determine its state and put into a glass bottle. After letting stand for 2 weeks at 50° C., evaluation was conducted. The stability was evaluated according to the following 3-grade scale:

The results are shown in Table 1. The units of the figures in the table are wt %.

◯: No change

Δ: Slight separation of the oil phase or the water phase was observed.

X: Substantial separation of the oil phase or the water phase was observed.

TABLE 1

|  | Comparative example 1 | Comparative example 2 | Comparative example 3 | Comparative example 4 | Example 1 | Example 2 | Example 3 | Example 4 | Example 5 | Example 6 | Example 7 |
|---|---|---|---|---|---|---|---|---|---|---|---|
| EC[1] | 0.25 | — | 0.25 | 0.25 | 0.25 | 1.0 | 0.1 | 2.0 | 0.25 | 0.25 | 0.25 |
| Ethanol | — | — | — | 0.5 | 0.5 | 2.0 | 0.5 | 5.0 | 0.5 | 0.5 | 0.5 |
| Methylphenyl polysiloxane | 5.0 | 5.0 | 5.0 | 5.0 | 5.0 | 5.0 | 5.0 | 5.0 | 5.0 | 5.0 | 5.0 |
| Decyltetra dodecanol | 5.0 | 5.0 | 5.0 | 5.0 | 5.0 | 5.0 | 5.0 | 5.0 | 5.0 | 5.0 | 5.0 |
| Isostearic acid | 5.0 | 5.0 | 5.0 | 5.0 | 5.0 | 5.0 | 5.0 | 5.0 | 5.0 | 5.0 | 5.0 |
| Glyceryl trioctanoate | 5.0 | 5.0 | 5.0 | 5.0 | 5.0 | 5.0 | 5.0 | 5.0 | 5.0 | 5.0 | 5.0 |
| CMC[2] | — | 2.0 | 2.0 | — | 0.5 | 0.5 | 2.0 | 1.0 | — | — | — |
| CC[3] | — | — | — | — | — | — | — | — | 0.45 | 0.4 | 0.8 |

TABLE 1-continued

|  | Comparative example 1 | Comparative example 2 | Comparative example 3 | Comparative example 4 | Example 1 | Example 2 | Example 3 | Example 4 | Example 5 | Example 6 | Example 7 |
|---|---|---|---|---|---|---|---|---|---|---|---|
| HA—Na[4] | — | — | — | — | — | — | — | — | 0.05 | 0.1 | 0.2 |
| Purified water | to 100 | to 100 | to 100 | to 100 | to 100 | to 100 | to 100 | to 100 | to 100 | to 100 | to 100 |
| Immediately ater emulsification | X | X | X | ◯ | ◯ | ◯ | ◯ | ◯ | ◯ | ◯ | ◯ |
| After 2 weeks at 50° C. | X | X | X | X | ◯ | ◯ | ◯ | ◯ | ◯ | ◯ | ◯ |

[1] Ethyl cellulose (N-22 from Hercules)
[2] Sodium carboxymethyl cellulose (Selogen-F8R from Daiichi Kogyo Seiyaku Co., Ltd.)
[3] Cationized cellulose (Polymer JR400 from Amerchol)
[4] Sodium hyaluronate (Byohyaluro 12 from Shiseido)

As shown in Table 1, when emulsification was conducted using EC or the water soluble polymer (CMC) solely (Comparative examples 1 and 2), separation was observed immediately after the emulsification and a stable W/O type emulsified composition was not obtained. As for the system prepared by dispersing EC directly in the oil phase without using ethanol and emulsifying this with the water soluble polymer (Comparative example 3), separation was observed immediately after emulsification, and the emulsified composition could not be obtained. In the case where only the water soluble polymer was omitted (Comparative example 4), an emulsified composition was obtained, but the stability was poor. On the other hand, Examples 1–7 of the present invention which contained EC, ethanol and the water soluble polymer or polyion complex produced W/O type emulsified compositions with excellent stability at each level.

EXAMPLE 8

Moisture Cream

|  |  | wt % |
|---|---|---|
| (A) | EC (N-22 from Hercules) | 0.25 |
|  | Ethanol | 2.0 |
|  | Methylphenyl polysiloxane | 5.0 |
|  | Glyceryl tri-2-ethylhexylate | 3.0 |
|  | Jojoba oil | 2.0 |
|  | Decyltetra decanol | 2.0 |
|  | Vitamin E acetate | 0.2 |
|  | Preservative | 0.1 |
| (B) | Glycerine | 10.0 |
|  | 1,3 butylene glycol | 5.0 |
|  | Sodium carboxymethyl cellulose (Selogen-FSR from Daiichi Kogyo Seiyaku Co. Ltd.) | 1.0 |
|  | Sodium hyaluronate (Biohyaluro 12 from Shiseido) | 0.1 |
|  | Purified water | Balance |

(Preparation method)

Phase (A) was homogeneously dissolved at 70° C. Phase (B), in which the water soluble polymer was homogeneously dispersed, was heated up to 70° C. and gradually added to phase (A) while stirring using a disper was conducted. After the addition was completed, emulsification using a disper at 5,000 rpm was conducted for 2 minutes and the mixture was stirred and cooled to obtain Example 8. The obtained moisture cream had superior stability over time, spread very well when applied to the skin, and exhibited ease of use without repulsion. Also, it was confirmed that there were no problems regarding its safety.

EXAMPLE 9

Night cream

|  |  | wt % |
|---|---|---|
| (A) | EC (N-50 from Hercules) | 0.05 |
|  | Ethanol | 0.1 |
|  | Liquid paraffin | 5.0 |
|  | Vaseline | 5.0 |
|  | Methylphenyl polysiloxane | 2.0 |
|  | Isostearyl alcohol | 5.0 |
|  | Macademia nut oil | 5.0 |
|  | Microcrystalline wax | 1.0 |
|  | Cetostearyl alcohol | 2.0 |
|  | Vitamin E acetate | 0.2 |
|  | Preservative | 0.1 |
| (B) | Glycerine | 5.0 |
|  | 1,3 butylene glycol | 5.0 |
|  | Carboxyvinyl polymer | 0.2 |
|  | Potassium hydroxide | 0.01 |
|  | Purified water | Balance |

(Preparation method)

Phase (A) was homogeneously dissolved at 70° C. The water soluble polymer was then homogeneously dissolved in this and the temperature was raised up to 70° C. Phase (B) was then gradually added to this while stirring using a disper was conducted. After the addition was completed, emulsification using a disper at 5,000 rpm was conducted for 2 minutes and the mixture was stirred and cooled to obtain Example 6. The obtained night cream had superior stability over time, spread very well when applied to the skin, and exhibited ease of use without repulsion. Also, it was confirmed that there were no problems regarding its safety.

EXAMPLE 10

Sunscreen cream

|  |  | wt % |
|---|---|---|
| (A) | EC (N-4 from Hercules) | 1.0 |
|  | Ethanol | 10.0 |
|  | 2-ethylhexyl succinate | 15.0 |
|  | Octylmethoxy cinnamate | 10.0 |
|  | 4-methoxy-4'-t-butylbenzoyl methane | 5.0 |
|  | Isotearic acid | 5.0 |
|  | Vitamin E acetate | 0.2 |
|  | Preservative | 0.1 |
|  | Perfume | 0.1 |
| (B) | 1,3 butylene glycol | 5.0 |
|  | Sodium carboxymethyl cellulose (Selogen-FSR from Daiichi Kogyo Seiyaku Co., Ltd.) | 1.0 |
|  | NaCl | 1.0 |
|  | Purified water | Balance |

(Preparation method)

Phase (A) was homogeneously dissolved at 70° C. Phase (B), in which the water soluble polymer was homogeneously dispersed, was heated up to 70° C. and gradually added to phase (A) while stirring using a disper was conducted. After the addition was completed, emulsification using a disper at 7,000 rpm was conducted for 2 minutes and the mixture was stirred and cooled to obtain Example 10. The obtained sunscreen cream had superior stability over time, spread very well when applied on the skin, and exhibited ease of use without repulsion. Having superior water resistance, it was a formulation system which be a fully effective sunscreen.

EXAMPLE 11

Sunscreen cream

| | | wt % |
|---|---|---|
| (A) | EC (N-4 from Hercules) | 0.25 |
| | Ethanol | 5.0 |
| | Cyclic polysiloxane | 5.0 |
| | Ethylhexyl 2-succinate | 5.0 |
| | Octylmethoxy cinnamate | 15.0 |
| | 4-methoxy-4'-t-butylbenzoyl methane | 1.0 |
| | Isotearic acid | 2.0 |
| | Hydrophobic titanium oxide | 10.0 |
| | Hydrophobic zinc oxide | 5.0 |
| | Vitamin E acetate | 0.2 |
| | Preservative | 0.1 |
| (B) | 1,3 butylene glycol | 5.0 |
| | Sodium carboxymethyl cellulose (Selogen FSR from Daiichi Kogyo Seiyaku Co., Ltd.) | 1.0 |
| | Sodium glutamate | 0.5 |
| | Purified water | Balance |

(Preparation method)

Phase (A) was homogeneously dissolved at 70° C. Phase (B), in which the water soluble polymer was homogeneously dispersed, was heated up to 70° C. and gradually added to phase (A) while stirring using a disper was conducted. After the addition was completed, emulsification using a disper at 7,000 rpm was conducted for 2 minutes and the mixture was stirred and cooled to obtain Example 11. The obtained suncare cream had superior stability over time, spread very well when applied on the skin, and exhibited ease of use without repulsion. Having superior water resistance, it was a formulation system which could be a fully effective sunscreen cream.

EXAMPLE 12

Hair treatment cream

| | | wt % |
|---|---|---|
| (A) | EC (N-4 from Hercules) | 0.25 |
| | Isopropyl alcohol | 5.0 |
| | Isoparaffin | 20.0 |
| | Silicon rubber | 1.0 |
| | Isotearic acid | 2.0 |
| (B) | Propylene glycol | 5.0 |
| | Cationized cellulose (Polymer JR400 from Amerchol) | 2.0 |
| | NaCl | 1.0 |
| | Purified water | Balance |

(Preparation method)

Phase (A) was homogeneously dissolved at 70° C. Phase (B), in which the water soluble polymer was homogeneously dispersed, was heated up to 70° C. and gradually added to phase (A) while stirring using a diaper was conducted. After the addition was completed, emulsification using a disper at 7,000 rpm was conducted for 2 minutes and the mixture was stirred and cooled to obtain Example 12. The obtained hair treatment cream had superior stability over time, spread very well when applied on the skin, and exhibited ease of use without repulsion.

EXAMPLE 13

Hair dye

| | | wt % |
|---|---|---|
| | (formulation 1) | |
| (A) | EC (N 50 from Hercules) | 0.5 |
| | Ethanol | 1.0 |
| | Methylphenyl polysiloxane | 15.0 |
| | Isostearyl alcohol | 5.0 |
| | Perfume | 0.05 |
| (B) | Propylene glycol | 5.0 |
| | Cationized cellulose (Polymer JR400 from Amerchol) | 2.0 |
| | p-phenylenediamine | 0.5 |
| | Resorcinol | 0.2 |
| | Monoethanol amine | 1.0 |
| | Chelating agent | Appropriate amount |
| | Preservative | Appropriate amount |
| | Purified water | Balance |
| (C) | Aqueous ammonia | 3.0 |
| | (Formulation 2) | |
| | Hydrogen peroxide (30%) | 20.0 |
| | Cetostearyl alcohol | 3.0 |
| | Sodium laurylsulfate | 0.5 |
| | POE cetyl ether | 0.5 |
| | pH regulator | Appropriate amount |
| | Preservative | Appropriate amount |
| | Ion-exchanged water | Balance |

(Preparation method)

Phase (A) was homogeneously dissolved at 70° C. Phase (B), having been homogeneously dissolved at room temperature, was gradually added to this while stirring using a disper was conducted, and then phase (C) was gradually added. After the addition was completed, emulsification using a disper at 5,000 rpm was conducted for 2 minutes to obtain Example 13. The obtained hair dye formulation 1 had superior stability over time and had superior hair dyeing characteristics when used with hair dye formulation 2 which was prepared separately with the recipe above. Also, it was confirmed that there were no problems regarding its safety.

EXAMPLE 14

Moisture cream

| | | wt % |
|---|---|---|
| (A) | EC (N-22 from Hercules) | 0.25 |
| | Ethanol | 0.5 |
| | Methylphenyl polysiloxane | 5.0 |
| | Glyceryl diisostearate | 2.0 |
| | Jojoba oil | 2.0 |
| | Isostearyl alcohol | 0.5 |
| | Vitamin E acetate | 0.5 |
| | Preservative | 0.1 |
| | Perfume | 0.1 |
| (B) | Glycerine | 10.0 |
| | 1,3 butylene glycol | 5.0 |
| | Cationized cellulose (Polymer JR400 from Amerchol) | 0.45 |
| | Sodium hyaluronate (Biohyaluro 12 from Shiseido) | 0.05 |
| | Purified water | Balance |

(Preparation method)

Phase (A) was homogeneously dissolved at 70 ° C. Phase (B), homogeneously mixed and heated up to 70° C., was gradually added to phase (A) while stirring using a disper was conducted. After the addition was completed, emulsification using a disper at 6,000 rpm was conducted for 2 minutes and the mixture was stirred and cooled to obtain Example 14. The obtained moisture cream had superior stability over time, spread very well when applied to the skin, and exhibited ease of use without repulsion. Also, it was confirmed that there were no problems regarding its safety.

EXAMPLE 15

Night cream

| | | wt % |
|---|---|---|
| (A) | EC (N-22 from Hercules) | 0.5 |
| | Ethanol | 2.0 |
| | Liquid paraffin | 1.0 |
| | Vaseline | 1.0 |
| | Methylphenyl polysiloxane | 10.0 |
| | Glyceryl trioctanoate | 5.0 |
| | Olive oil | 5.0 |
| | Isotearic acid | 2.0 |
| | Cetostearyl alcohol | 0.1 |
| | Vitamin E acetate | 0.5 |
| | Preservative | 0.1 |
| | Perfume | 0.1 |
| (B) | Glycerine | 5.0 |
| | 1,3 butylene glycol | 5.0 |
| | Cationized cellulose (Polymer JR400 from Amerchol) | 0.4 |
| | Na hyaluronate (Biohyaluro 12 from Shiseido) | 0.1 |
| | Purified water | Balance |

(Preparation method)

The preparation method is the same as in Example 4. The obtained night cream had superior stability over time, spread very well when applied to the skin, and exhibited ease of use without repulsion. Also, it was confirmed that there were no problems regarding its safety.

EXAMPLE 16

Suncare cream

| | | wt % |
|---|---|---|
| (A) | EC (N-50 from Hercules) | 1.0 |
| | Ethanol | 5.0 |
| | Vaseline | 1.0 |
| | Methylphenyl Polysiloxane | 5.0 |
| | Decamethyl cyclopentasiloxane | 5.0 |
| | Octylmethoxy cinnamate | 10.0 |
| | Isostearyc acid | 3.0 |
| | 2-octyl dodecanol | 2.0 |
| | Vitamin E acetate | 0.5 |
| | Preservative | 0.1 |
| | Perfume | 0.1 |
| (B) | Glycerine | 5.0 |
| | Cationized cellulose (Polymer JR400 from Amerchol) | 0.8 |
| | Na hyaluronate (Biohyaluro 12 from Shiseido) | 0.2 |
| | Purified water | Balance |

(Preparation method)

While a homogenizer was used for stirring, octyl cinnamate was added to homogeneously mixed (B) phase to prepare an O/W emulsified composition. This emulsion was then heated up to 70° C. and gradually added to the rest of (A) phase, homogeneously dissolved at 70° C., while stirring using a disper was conducted to obtain Example 16. The obtained suncare cream had superior stability over time, spread very well when applied on the skin, and exhibited ease of use without repulsion.

What is claimed is:

1. A water-in-oil (W/O) emulsified composition comprising an oil phase containing ethyl cellulose and an ethyl cellulose swelling solvent, and a water phase containing a water soluble polymer(s) which has been emulsified without a surfactant.

2. The W/O emulsified composition of claim 1 wherein said ethyl cellulose swelling solvent is one or more types of solvent selected from the group consisting of methanol, ethanol, propanol, isopropanol, isobutyl alcohol, benzyl alcohol and acetone.

3. The W/O emulsified composition of claim 1 wherein the amount of said ethyl cellulose added is 0.01 to 10 wt % of the total W/O emulsified composition, the amount of said ethyl cellulose swelling solvent added is 0.01 to 20 wt % of the total W/O emulsified composition, and the amount of said water soluble polymer added is 0.1 to 10 wt % of the total W/O emulsified composition.

4. A water in oil (W/O) emulsified composition comprising an oil phase containing ethyl cellulose and an ethyl cellulose swelling solvent, and a water phase containing a polyion complex comprising cationized cellulose and sodium hyaluronate which has been emulsified without a surfactant.

5. The W/O emulsified composition of claim 4 wherein said ethyl cellulose swelling solvent is one or more types of solvent selected from the group consisting of methanol, ethanol, propanol, isopropanol, isobutyl alcohol, benzyl alcohol and acetone.

6. The W/O emulsified composition of claim 4 wherein the amount of said ethyl cellulose added is 0.01 to 10 wt % of the total W/O emulsified composition, the amount of said ethyl cellulose swelling solvent added is 0.01 to 20 wt % of the total W/O emulsified composition, and the amount of said polyion complex added is 0.1 to 10 wt % of the total W/O emulsified composition.

7. A method of manufacturing a water in oil (W/O) emulsified composition in which an oil phase containing ethyl cellulose is prepared by using an ethyl cellulose swelling solvent and then said oil phase and a water phase containing a water soluble polymer are stirred without using a surfactant to emulsify them as a water-in-oil (W/O) emulsion.

8. A method of manufacturing a water in oil (W/O) emulsified composition in which an oil phase containing ethyl cellulose is prepared by using an ethyl cellulose swelling solvent and then said oil phase and a water phase containing a polyion complex comprising cationized cellulose and sodium hyaluronate are stirred without using a surfactant to emulsify them as a water-in-oil (W/O) emulsion.

9. A W/O emulsified cosmetic comprising the W/O emulsified composition of claim 1.

10. A W/O emulsified cosmetic comprising the W/O emulsified composition of claim 4.

* * * * *